United States Patent [19]

Hefner, Jr.

[11] Patent Number: 4,487,915

[45] Date of Patent: Dec. 11, 1984

[54] HYDROXY AROMATIC OLIGOMERS CONTAINING TRIAZINE AND OXAZOLINE GROUPS AND EPOXY RESINS PREPARED THEREFROM

[75] Inventor: Robert E. Hefner, Jr., Lake Jackson, Tex.

[73] Assignee: The Dow Chemical Company, Midland, Mich.

[21] Appl. No.: 576,304

[22] Filed: Feb. 2, 1984

[51] Int. Cl.$^3$ .............................................. C08G 59/26
[52] U.S. Cl. .................................... 528/96; 252/182; 544/219
[58] Field of Search ................ 528/96; 544/193, 219; 252/182

[56] References Cited

U.S. PATENT DOCUMENTS

| | | | |
|---|---|---|---|
| 2,741,607 | 4/1956 | Bradley et al. | 260/248 |
| 2,809,942 | 10/1957 | Cooke, Jr. | 260/2 |
| 2,810,706 | 10/1957 | Frazier et al. | 260/45.5 |
| 2,864,805 | 12/1958 | Cooke, Jr. | 260/47 |
| 2,971,942 | 2/1961 | Masters et al. | 260/2 |
| 3,676,397 | 7/1972 | Clarke | 528/96 |
| 3,708,483 | 1/1973 | Anderson et al. | 260/248 CS |

FOREIGN PATENT DOCUMENTS 56-26925  3/1981  Japan.

*Primary Examiner*—Earl A. Nielsen
*Attorney, Agent, or Firm*—J. G. Carter

[57] ABSTRACT

The subject oligomers are prepared by reacting a diphenol with a cyanogen halide in the presence of an alkaline agent. The resultant product is then reacted with an epoxy resin thereby producing a hydroxy aromatic oligomers containing triazine and oxazoline groups. An epoxy resin is then prepared by reacting the previously formed oligomers with an epihalohydrin followed by dehydrohalogenation of the resultant product.

18 Claims, No Drawings

HYDROXY AROMATIC OLIGOMERS CONTAINING TRIAZINE AND OXAZOLINE GROUPS AND EPOXY RESINS PREPARED THEREFROM

BACKGROUND OF THE INVENTION

The present invention provides novel hydroxyaromatic oligomers containing both triazine and oxazoline groups, as well as epoxy resin compositions prepared from said oligomers.

Epoxy resins containing triazine groups are known from Japan Kokai Tokkyo Koho 81 26,925 dated March 16, 1981. However, the preparation of said resins involves the use of the difficult-to-obtain intermediate 2,4,6-trichloro-1,3,5-triazine. Furthermore, coupling of 2,4,6-trichloro-1,3,5-triazine with a diphenol through the chloride groups is difficult and leads to a relatively uncontrollable product mix.

An improved preparation of epoxy resins containing triazine groups is disclosed by Hefner, Jr. (in application Ser. No. 547,537 filed Oct. 31, 1983. The process of this invention uses an easily prepared mixed cyanate of a polyphenol More specifically, the diphenol, such as 4,4'-isopropylidenediphenol (Bisphenol A) is reacted with less than a stoichiometric equivalent of a cyanogen chloride or bromide in the presence of an alkaline agent, such as triethylamine. This provides a mixture of monocyanate, dicyanate, and optionally, unreacted diphenol. Trimerization of this mixture provides hydroxyaromatic oligomers containing the triazine group. The oligomers and unreacted diphenol, if any, are then epoxidized using methods well known in the art. Excellent control over the molecular weight and content of triazine groups is provided by this process. The epoxy resin compositions of this invention possess unusually high thermal stability, however, there is room for improvement in their mechanical properties, specifically tensile strength and elongation.

The hydroxyaromatic oligomers of the present invention contain both triazine and oxazoline groups. The oligomers are prepared by co-oligomerization of a mixed cyanate of a polyphenol with an epoxy resin in the process of the present invention. In the process, the diphenol, such as 4,4'-isopropylidenediphenol (Bisphenol A) is reacted with less than a stoichiometric equivalent of a cyanogen halide in the presence of an alkaline agent, such as triethylamine. This provides a mixture of monocyanate, dicyanate and, optionally, unreacted diphenol. Co-oligomerization of this mixture with the desired amount of an epoxy resin, such as the diglycidyl ether of Bisphenol A, provides hydroxyaromatic oligomers containing both triazine and oxazoline groups. Epoxidation of the oligomers and unreacted diphenol, if any, using methods well known in the art provides the epoxy resin compositions of this invention.

Although included within the scope of this invention, oligomers prepared from co-oligomerization of the mixed cyanate of a diphenol with an epoxy resin wherein the mole ratio of epoxy groups to cyanate groups is less than about 1:10, respectively, are generally insoluble in solvent(s) and/or reactant(s) useful in epoxidation reactions but are useful as thermoset resins. Oligomers prepared from co-oligomerization of the mixed cyanate of a diphenol with an epoxy resin wherein the mole ratios of epoxy groups to cyanate groups are about 1:10 to about 1:40 are most preferred precursors to the epoxy resins of the present invention.

Unreacted diphenol (polyphenol), which is preferably present as a component of the oligomers, is converted to the corresponding diglycidyl ether during the epoxidation of the hydroxyaromatic oligomers. This improves overall processability of the epoxy resin. If desired, extra diphenol can be added prior to epoxidation to increase the diphenol diglycidyl ether content of the finished epoxy resin product. Likewise, extra dicyanate may be added to the cyanate mixture prior to co-oligomerization with an epoxy resin.

SUMMARY OF THE INVENTION

The present invention pertains to hydroxyaromatic oligomer compositions containing both triazine and oxazoline groups. Said hydroxyaromatic oligomer compositions (I) are prepared by reacting (A) at least one material having an average of more than one aromatic hydroxyl group per molecule with (B) at least 0.01 but not more than 0.95, preferably from about 0.05 to about 0.55, moles of cyanogen halide or mixture of cyanogen halides per aromatic hydroxyl group in the presence of (C) a suitable base in a quantity of from about 0.01 to about 1.1, preferably from about 0.05 to about 0.6, moles per aromatic hydroxyl group at a temperature and time sufficient to essentially complete the reaction and thereafter recovering the resultant cyanate mixture; (II) co-oligomerizing the product resulting from (I) with an epoxy resin wherein the mole ratio of epoxy groups to cyanate groups is from about 1:1 to about 1:100, preferably from about 1:10 to about 1:40 in the presence of a suitable co-oligomerization catalyst at a temperature and time to essentially complete the co-oligomerization reaction.

Another aspect of the present invention pertains to epoxy resin compositions containing both triazine and oxazoline groups. Said epoxy resin compositions (III) are prepared by epoxidizing the resultant co-oligomerization product from step (II) in a conventional manner by reaction with an epihalohydrin with subsequent dehydrohalogenation with a basic-acting material and finally recovering the resultant glycidyl ether product.

Another aspect of the present invention pertains to the product resulting from curing a composition comprising the aforementioned epoxy resin and a curing quantity of a catalyst and/or curing agent therefor.

DETAILED DESCRIPTION OF THE INVENTION

Suitable materials having an average of more than one aromatic hydroxyl group per molecule which can be employed in the present invention include, for example, those represented by the formulas

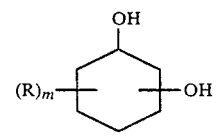

I

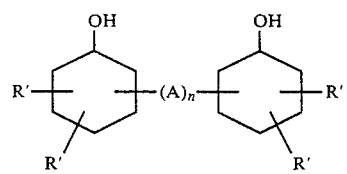

II

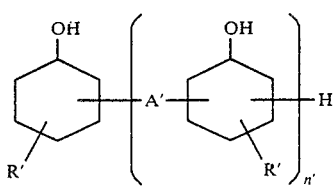

wherein A is a divalent hydrocarbon group having from 1 to about 12, preferably from about 1 to about 6 carbon atoms, —S—, —S—S—,

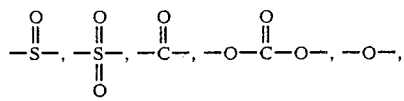

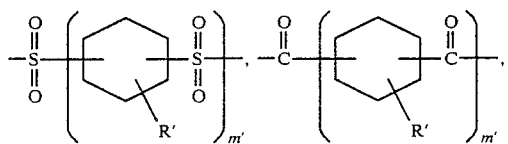

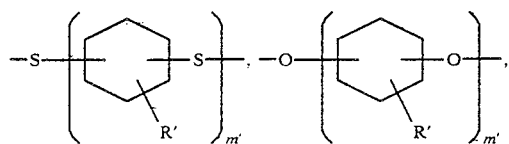

and the like; each A' is a divalent hydrocarbon group having from 1 to about 3, preferably 1, carbon atoms; each R is independently hydrogen, halogen, preferably chlorine or bromine, a hydrocarbyl group having from 1 to about 6 carbon atoms or a hydroxyl group; each R' is independently hydrogen or a hydrocarbyl group having from 1 to about 6 carbon atoms or a halogen, preferably chlorine or bromine; m has a value from zero to about 2; m' has a value from 1 to about 100; n has a value of zero or 1 and n' has a value from about 1.01 to about 6.

Particularly suitable aromatic hydroxyl-containing compounds include, for example, o-, m- and p-dihydroxybenzene, 2-tert butyl hydroquinone, 2,4-dimethyl resorcinol, 2,5-di-tert butyl hydroquinone, tetramethyl hydroquinone, 2,4,6-trimethyl resorcinol, 4-chlororesorcinol, 4-tert butyl pyrocatechol, 1,1-bis(4-hydroxyphenyl)ethane; 2,2-bis(4-hydroxyphenyl)propane; 2,2-bis(4-hydroxyphenyl)-pentane; bis(4,4'-dihydroxyphenyl)methane; 4,4'-dihydroxydiphenyl, 2,2'-dihydroxydiphenyl, 3,3',5,5'-tetramethyl-4,4'-dihydroxydiphenyl, 3,3',5,5'-tetrachloro-4,4'-dihydroxydiphenyl, 3,3',5,5'-tetrachloro-2,2'-dihydroxydiphenyl, 2,2',6,6'-tetrachloro-4,4'-dihydroxydiphenyl, 4,4'-bis((3-hydroxy)phenoxy)-diphenyl, 4,4'-bis((4-hydroxy)phenoxy)-diphenyl, 2,2'-dihydroxy-1,1'-binaphthyl, and other dihydroxydiphenyls; 4,4'-dihydroxydiphenyl ether, 3,3',5,5'-tetramethyl-4,4'-dihydroxydiphenyl ether, 3,3',5,5'-tetrachloro-4,4'-hydroxydiphenyl ether, 4,4'-bis(p-hydroxyphenoxy)-diphenyl ether, 4,4'-bis(p-hydroxyphenyl isopropyl)-diphenyl ether, 4,4'-bis(p-hydroxyphenoxy)-benzene, 4,4'-bis(p-hydroxyphenoxy)-diphenyl ether, 4,4'-bis(4(4-hydroxyphenoxy)phenyl sulfone)-diphenyl ether, and other dihydroxydiphenyl ethers; 4,4'-dihydroxydiphenyl sulfone, 3,3',5,5'-tetramethyl-4,4'-dihydroxydiphenyl sulfone, 3,3'5,5'tetrachloro-4,4'dihydroxydiphenyl sulfone, 4,4'-bis(p-hydroxyphenyl isopropyl)-diphenyl sulfone, 4,4'-bis((4-hydroxy)-phenoxy)-diphenyl sulfone, 4,4'-bis((3-hydroxy)phenoxy)-diphenyl sulfone, 4,4'-bis(4-(4-hydroxyphenylisopropyl)-phenoxy)-diphenyl sulfone, 4,4'-bis(4(4-hydroxy)diphenoxy)-diphenyl sulfone, and other diphenyl sulfones; 4,4'-dihydroxydiphenyl methane, 4,4'-bis(p-hydroxyphenyl)-diphenyl methane, 2,2'-bis(p-hydroxyphenyl)propane, 3,3',5,5'-tetramethyl-2,2'-bis(p-hydroxyphenyl)propane, 3,3',5,5,'-tetrachloro-2,2'-bis(p-hydroxyphenyl)propane, 1,1-bis(p-hydroxyphenyl)-cyclohexane, bis-(2-hydroxy-1-naphthyl)-methane, 1,2-bis(p-hydroxyphenyl)-1,1,2,2-tetramethyl ethane, 4,4'-dihydroxybenzophenone, 4,4'-bis(4-hydroxy)phenoxy-benzophenone, 1,4-bis(p-hydroxyphenyl isopropyl)-benzene, phloroglucinol, pyrogallol, 2,2',5,5'-tetrahydroxy-diphenyl sulfone, other dihydroxydiphenyl alkanes, mixtures thereof and the like.

Suitable cyanogen halides which can be employed herein include, for example, cyanogen chloride, cyanogen bromide, mixtures thereof and the like.

If desired, the method reported in Organic Syntheses, Vol. 61, page 35–37 (1983), published by John Wiley & Sons, may be used to generate the required amount of cyanogen halide in situ, although this is less preferred than using neat cyanogen halide.

Suitable base materials which can be employed herein as component (I-C) include both inorganic bases and tertiary amines such as, for example, sodium hydroxide, potassium hydroxide, triethylamine, mixtures thereof and the like. The tertiary amines are most preferred as the base material.

Suitable epoxy resins for co-oligomerization with the cyanate mixture include, for example, those represented by the formulas

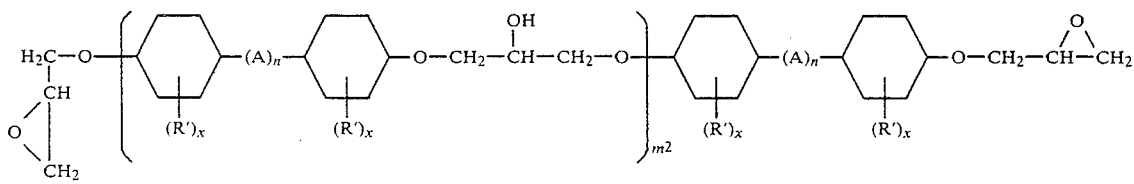

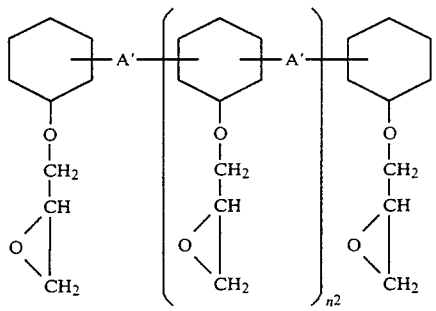

wherein A, R' and n are as hereinbefore defined, and $m^2$ has an average value of from zero to about 40, preferably from about 0.01 to about 10,; $n^2$ has a value of 0.001 to about 10, preferably from about 1 to about 5 and x has a value of 4.

Suitable co-oligomerization catalysts which can be employed herein include, for example, metal salts of carboxylic acids, such as, lead octoate, zinc stearate, zinc acetylacetonate, at concentrations of about 0.001 to 5 percent. Most preferred catalysts are cobalt naphthenate and cobalt octoate, mixtures thereof and the like.

Although the co-oligomerization of the cyanate mixture with the epoxy resin provides both triazine and oxazoline functionality in the oligomer product, it is felt that other reactions may also be occurring. For example, unreacted phenolic groups may react with cyanate groups to form iminocarbonate linkages which may in turn react with remaining epoxide groups.

The epoxidation, step III, can be employed by the known methods described in *Handbook of Epoxy Resins* by Lee and Neville, McGraw-Hill, 1967 which is incorporated herein by reference. This usually includes reacting the product from step (II) with an epihalohydrin followed by dehydrohalogenation with a basic-acting material such as an alkali metal hydroxide and finally recovering the resultant glycidyl ether product.

Suitable curing agents and/or catalysts for the epoxy resins are described in the aforementioned *Handbook of Epoxy Resins*.

The step (I) reaction is usually conducted at a temperature of from about −40° C. to about 60° C., preferably from about −20° C. to about 25° C. for from about 10 minutes (600 s) to about 120 minutes (7200 s), preferably from about 10 minutes (600 s) to about 60 minutes (3600 s).

If desired, the reaction of step (I) can be conducted in the presence of an inert solvent reaction medium. Suitable such solvents include, for example, water, chlorinated hydrocarbons, ketones, mixtures thereof and the like. Acetone, chloroform, and methylene chloride are most preferred as solvents.

The reaction of step (II) is usually conducted at a temperature of from about 70° C. to about 350° C., preferably from about 70° C. to about 200° C. for a period of from about 15 minutes (900 s) to about 120 minutes (7200 s), preferably from about 30 minutes (1800 s) to about 75 minutes (4500 s). The reaction is preferably performed in the presence of a suitable co-oligomerization catalyst.

The epoxy resins of the present invention can be used to prepare, castings, coatings, laminates, encapsulations and the like, and are especially suited for use in high temperature environments and where high mechanical strength is required.

The following examples are illustrative of the invention, but are not to be construed as to limiting the scope thereof in any manner.

EXAMPLE 1

A. Preparation of Diphenol Cyanate Mixture

Cyanogen bromide (0.55 moles, 58.26 grams) was added to a reactor containing stirred acetone (175 milliliters) under a nitrogen atmosphere. The cyanogen bromide-acetone solution was cooled to −3° C., then Bisphenol A (1.00 mole, 228.30 grams) dissolved in chilled acetone (650 milliliters) was added to the reactor. The stirred solution was allowed to equilibrate at −3° C., then triethylamine (0.50 mole, 50.60 grams) was added to the reactor over a thirty minute (1800 s) period so as to maintain the reaction temperature at −5° to 0° C. After completion of the triethylamine addition, the reactor was maintained at 0° to 7° C. for an additional 20 minutes (1200 s), followed by addition of the reaction product to chilled water (1 gallon, 3078 ml) with agitation. After 15 minutes (900 s), the water and product mixture was multiply extracted with methylene chloride (400 milliliters total). The combined methylene chloride extracts were washed 5 percent hydrochloric acid (500 milliliters), then water (800 milliliters), and then dried over anhydrous sodium sulfate. The dry methylene chloride extract was filtered and solvent removed by rotary evaporation under vacuum. The diphenol cyanate mixture was recovered (234.12 grams) as a white-colored solid at room temperature (25° C). Infrared spectrophotometric analysis demonstrated the presence of the cyanate functionality as well as unreacted hydroxyl functionality. Liquid chromatographic analysis demonstrated the presence of 67.2 area percent Bisphenol A, 29.9 area percent Bisphenol A monocyanate, and 2.9 area percent Bisphenol A dicyanate.

B. Co-oligomerization of Diphenol Cyanate Mixture and an Epoxy Resin

A portion of the diphenol cyanate mixture (230.3 grams) from A above, an epoxy resin (10.79 grams) and 6.0 percent cobalt naphthenate (0.10 percent by weight, 0.24 gram) were thoroughly mixed and placed in a glass tray. The epoxy resin had an epoxide equivalent weight (EEW) of 337.8 and was prepared by reaction of Bisphenol A diglycidyl ether, EEW=183, (0.40 mole, 146.4 grams) with Bisphenol A (0.20 mole, 45.66 grams) and benzyl trimethylammonium chloride catalyst 60 percent aqueous, (0.19 gram) at 120° C. for 50 minutes (3000 s). The tray was then placed in a forced-air, convection-type oven and maintained for 1.25 hours (4500 s) at 177° C. The hydroxyaromatic co-oligomerization product containing triazine and oxazoline groups was recovered in quantitative yield as a transparent, light amber-colored, brittle solid at room temperature (25° C.). Infrared spectrophotometric analysis demonstrated complete disappearance of the cyanate functionality, appearance of the triazine functionality, appearance of the oxazoline functionality and the presence of unreacted hydroxyl functionality.

C. Epoxidation of Hydroxyaromatic Co-oligomerization Product Containing Triazine and Oxazoline Groups A portion of the hydroxyaromatic co-oligomerization product containing triazine nd oxazoline groups (215.0 grams), epichlorohydrin (7.602 moles, 703.41 grams), isopropanol (35 percent by weight of epichlorohydrin used, 378.76 grams), and water (8 percent by weight of epichlorohydrin used, 61.16 grams) were added to a reactor and stirred under a nitrogen atmosphere at 50° C. until a solution was formed. At that time, dropwise addition of a sodium hydroxide (2.74 moles, 109.47 grams) solution in water (437.88 grams) commenced and was completed over the next 45 minutes (2700 s). During this sodium hydroxide addition, the reaction temperature was allowed to increase to 60° C. and was then held at this temperature. Fifteen minutes (900 s) after the addition of sodium hydroxide solution, a second solution of sodium hydroxide (1.22 mole 48.65 grams) in water (194.61 grams) was added dropwise to the reactor over the next 20 minutes (1200 s). Fifteen minutes (900 s) later, the reactor was cooled to 40° C., then an initial water wash (400 milliliters) was added to the reactor. The reactor contents were transferred to a separatory funnel containing additional epichlorohydrin (200 milliliters). The water wash layer was separated and discarded while the organic layer was added back into the separatory funnel along with a second water wash (200 milliliters). The organic layer was separated then added back into the separatory funnel along with a third water wash (800 milliliters) and additonal epichlorohydrin (200 milliliters). The recovered organic layer was stripped of solvents by rotary evaporation at 100° C. for 30 minutes (1800 s) under vaccuum. The epoxy resin was recovered (301.91 grams) as a transparent, light amber-colored liquid at room temperature (25° C.). Infrared spectrophotometric analysis demonstrated substantially complete disappearance of hydroxyl functionality, appearance of epoxide functionality and presence of both triazine and oxazoline functionalities. Epoxide titration revealed the presence of 20.82 percent by weight epoxide.

EXAMPLE 2

A portion of the epoxy resin of Example 1C (285.0 grams) was heated to 75° C., then methylenedianiline (68.31 grams) was added and thoroughly mixed in. This solution was used to prepare a clear, unfilled one-eighth inch (0.3175 cm) casting for heat distortion temperature (264 psi, 1820 kPa), tensile and flexural strength, flexural modulus, percent elongation, average Barcol hardness (934-1 scale) and unnotched Izod impact strength determinations. The casting was cured for 2 hours (7200 s) at 75° C., followed by post-curing for 2 hours (7200 s) at 125° C., 2 hours (7200 s) at 175° C., then 2 hours (7200 s) at 200° C. Mechanical properties of tensile (8) and flexural (5) test pieces were determined using an Instron machine with standard test methods (ASTM D638 and D790). Heat distortion temperature of clear casting test pieces (2) was determined using an Aminco Plastic Deflection Tester (American Instrument Co.) with standard test methods (ASTM D648). Nine 2.5 ×0.5 ×0.125 inch (6.35 ×1.27 ×0.3125 cm) test pieces were prepared from the clear, unfilled casting and tested for unnotched Izod impact using a TMI impact Tester No. 43-1 with standard test method (ASTM D 256). The results are reported in Table I.

TABLE I

| | |
|---|---|
| Average Barcol Hardness | 40 |
| Heat Distortion Temperature (°F./°C.) | 296/147 |
| Tensile Strength, | |
| psi | 12,593 |
| MPa | 87 |
| Elongation (%) | 5.36 |
| Flexural Strength, | |
| psi | 23,081 |
| MPa | 159 |
| Flexural Modulus, | |
| psi | 512,000 |
| MPa | 3528 |
| Izod Impact Strength, unnotched, | |
| ft-lb/in | 8.35 |
| J/cm | 4.46 |

COMPARATIVE EXPERIMENT A

A. Preparation of Diphenol Cyanate Mixture

Cyanogen bromide (0.55 moles, 58.26 grams) was added to a reactor containing stirred acetone (175 milliliters) under a nitrogen atmosphere. The cyanogen bromide-acetone solution was cooled to −5° C., then Bisphenol A (1.00 mole, 228.30 grams) dissolved in chilled acetone (650 milliliters) was added to the reactor. The stirred solution was allowed to equilibrate at −5° C., then triethylamine (0.50 mole, 50.60 grams) was added to the reactor over a 25 minute (1500 s) period and so as to maintain the reaction temperature at −2° to −5° C. After completion of the triethylamine addition, the reactor was maintained at −2° to 0° C. for an additional 20 minutes (1200 s), followed by addition of the reaction product to chilled water (1 gallon, 3078 ml) with agitation. After 15 minutes (900 s), the water and product mixture was multiply extracted with methylene chloride. The combined methylene chloride extracts were sequentially washed with dilute hydrochloric acid (5 percent), water, hydrochloric acid, water and then dried over anhydrous magnesium sulfate. The dry methylene chloride extract was filtered and solvent removed by rotary evaporation under vacuum. The diphenol cyanate mixture was recovered (229.7 grams) as a white-colored solid at room temperature (25° C.). Infrared spectrophotometric analysis demonstrated the presence of the cyanate functionality as well as unreacted hydroxyl functionality. Liquid chromatographic analysis demonstrated the presence of 55.82 area percent Bisphenol A, 37.89 area percent Bisphenol A monocyanate, and 6.29 area percent Bisphenol A dicyanate.

B. Trimerization of Diphenol Cyanate Mixture

The diphenol cyanate mixture (229.7 grams) and 6.0 percent cobalt naphthenate (0.10 percent by weight, 0.23 gram) were thoroughly mixed and placed in a glass tray. The tray was then placed in a forced-air, convection-type oven and maintained for 1.25 hour at 177° C.

The hydroxyaromatic oligomers containing triazine groups were recovered in quantitative yield as a transparent, brittle solid at room temperature (25° C.). The oligomers had a greenish-colored cast due to the catalyst. At the 177° C. temperature, the oligomers were still totally fluid. Infrared spectrophotometric analysis demonstrated complete disappearance of the cyanate functionality, appearance of the triazine functionality, and the presence of unreacted hydroxyl functionality.

C. Epoxidation of Hydroxy Aromatic Oligomers Containing Triazine Groups

A portion of the hydroxyaromatic oligomers containing triazine groups (215.00 grams), epichlorohydrin (6.865 moles, 635.22 grams), isopropanol (35 percent by weight of epichlorohydrin used, 342.04 grams), and water (8 percent by weight of epichlorohydrin used, 55.24 grams) were added to a reactor and stirred under a nitrogen atmosphere at 60° C. until a solution was formed. At this time, the reactor was cooled to 50° C. and dropwise addition of a sodium hydroxide (2.4714 moles, 98.86 grams) solution in water (395.42 grams) commenced and was completed over the next 45 minutes (2700 s). During this sodium hydroxide addition, the reaction temperature was allowed to increase to 60° C. and was then held at this temperature. Fifteen minutes (900 s) after the addition of sodium hydroxide solution, a second solution of sodium hydroxide (1.0984 mole, 43.94 grams) in water (175.76 grams) was added dropwise to the reactor over the next 20 minutes (1200 s). Fifteen minutes (900 s) later, the reactor was cooled to 40° C. then an initial water wash (400 grams) was added to the reactor. The reactor contents were transferred to a separatory funnel containing additional epichlorohydrin (200 grams). The water wash layer was separated and discarded while the organic layer was added back into the separatory funnel along with a second water wash (200 grams). The organic layer was separated then added back into the separatory funnel along with a third water wash (200 grams). The water wash layer was separated and discarded while the organic layer was added back into the separatory funnel with a final wash (1000 grams). Epichlorohydrin (200 grams) was added to the separatory funnel, then the water wash layer was separated and discarded. The recovered organic layer was stripped of solvents by rotary evaporation at 100° C. for 30 minutes (1800 s) under vacuum. The epoxy resin was recovered (272.4 grams) as a transparent, light yellow-colored liquid at room temperature (25° C.). Infrared spectrophotometric analysis demonstrated substantially complete disappearance of hydroxyl functionality, appearance of epoxide functionality and presence of triazine functionality. Epoxide titration revealed the presence of 21.55 percent by weight epoxide.

COMPARATIVE EXPERIMENT B

A portion of the epoxy resin of Comparative Experiment A-C (265.0 grams) was heated to 75° C., then methylenedianiline (65.74 grams) was added and thoroughly mixed in. This solution was used to prepare a clear, unfilled, one-eighth inch (0.3175 cm) casting using the method of Example 2. Mechanical property testing was completed using the method of Example 2 and the results are reported in Table II.

TABLE II

| Average Barcol Hardness | 42 |

TABLE II-continued

| Heat Distortion Temperature (°F./°C.) | 307/152.75 |
|---|---|
| Tensile Strength, | |
| psi | 10,694 |
| MPa | 74 |
| Elongation (%) | 3.69 |
| Flexural Strength, | |
| psi | 21,709 |
| MPa | 150 |
| Flexural Modulus, | |
| psi | 519,000 |
| MPa | 3576 |
| Izod Impact Strength, unnotched, | |
| ft-lb/in | 8.24 |
| J/cm | 4.4 |

EXAMPLE 3

Portions of the hydroxyaromatic co-oligomerization product containing triazine and oxazoline groups from Example 1-B and the hydroxyaromatic oligomers containing triazine groups from Comparative Experiment A-B were analyzed by gel permeation chromatography using polystyrene standards. The results are reported in Table III wherein the polydispersity ratio is defined as the ratio of the weight average to number average molecular weights.

TABLE III

| | Weight Average Molecular Weight | Polydispersity Ratio |
|---|---|---|
| Example 1-B | 7937 | 4.24 |
| Comparative Experiment A-B | 3748 | 1.40 |

EXAMPLE 4

A. Preparation of Diphenol Cyanate Mixture

Cyanogen bromide (0.55 moles, 58.26 grams) was added to a reactor containing stirred acetone (175 milliliters) under a nitrogen atmosphere. The cyanogen bromide-acetone solution was cooled to −4° C., then Bisphenol A (1.00 mole, 228.30 grams) dissolved in chilled acetone (650 milliliters) was added to the reactor. The stirred solution was allowed to equilibrate at −4° C., then triethylamine (0.50 mole, 50.60 grams) was added to the reactor over a 25 minute (1500 s) period and so as to maintain the reaction temperature at −2 to −5° C. After completion of the triethylamine addition, the reactor was maintained at −3° to −5° C. for an additional 20 minutes (1200 s), followed by addition of the reaction product to chilled water (1 gallon, 13.78 l) with agitation. After 15 minutes (900 s), the water and product mixture was multiply extracted with methylene chloride (400 milliliters total). The combined methylene chloride extracts were washed with 5 percent hydrochloric acid (500 milliliters), then water (800 milliliters), and then dried over anhydrous sodium sulfate. The dry methylene chloride extract was filtered and solvent removed by rotary evaporation under vacuum. The diphenol cyanate mixture was recovered (229.8 grams) as a white-colored solid at room temperature (25° C.). Infrared spectrophotometric analysis demonstrated the presence of the cyanate functionality as well as unreacted hydroxyl functionality. Liquid chromatographic analysis demonstrated the presence of 55.5 area percent Bisphenol A, 37.7 area Bisphenol A monocyanate, and 6.8 area percent Bisphenol A dicyanate.

B. Co-oligomerization of Diphenol Cyanate Mixture and an Epoxy Resin

A portion of the diphenol cyanate mixture (229.0 grams), an epoxy resin (153.29 grams) and 6.0 percent cobalt (0.10 percent by weight, 0.38 gram) were thoroughly mixed and placed in a glass tray. The epoxy resin used was identical to that described in Example 1-B. The tray was then placed in a forced-air, convection-type oven and maintained for 1.25 hours (4500 s) at 177° C. The hydroxyaromatic co-oligomerization product containing triazine and oxazoline groups was recovered in quantitative yield as a tan-colored, rigid, opaque solid at room temperature (25° C.). The product behaved as a rubbery solid at the 177° C. temperature. A lack of solubility in organic solvents precluded further analysis of the product.

EXAMPLE 5

A sample (9.56 milligrams) of the clear, unfilled casting of Example 2 was analyzed by thermogravimetric analysis (TGA) using a nitrogen flow rate of 80 cubic centimeters per minute and a rate of temperature increase of 10° C. per minute. The weight of the sample as a function of temperature is reported in Table IV.

COMPARATIVE EXPERIMENT C

A sample (14.98 milligrams) of the clear, unfilled casting of Comparative Experiment B was analyzed by thermogravimetric analysis (TGA) using the method of Example 5. The results are reported in Table IV.

TABLE IV

| Temperature (°C.) | Percent of Original Weight | |
| --- | --- | --- |
|  | Example 5 | Comparative Experiment C |
| 200 | 99.5 | 99.6 |
| 250 | 99.2 | 99.2 |
| 300 | 98.8 | 98.9 |
| 350 | 98.2 | 97.0 |
| 400 | 95.0 | 66.8 |
| 450 | 43.2 | 31.4 |
| 500 | 20.8 | 24.8 |

I claim:

1. Hydroxyaromatic oligomer compositions containing both triazine and oxazoline groups prepared by reacting (A) at least one material having an average of more than one aromatic hydroxyl group per molecule with (B) at least 0.01 but not more than 0.95 moles of cyanogen halide or mixture of cyanogen halides per aromatic hydroxyl group in the presence of (C) a suitable base in a quantity of from about 0.01 to about 1.1 moles per aromatic hydroxyl group at a temperature and time sufficient to essentially complete the reaction and thereafter recovering the resultant cyanate mixture; (II) co-oligomerizing the product resulting from (I) with (D) an epoxy resin wherein the mole ratio of epoxy groups to cyanate groups is about 1:1 to about 1:100 in the presence of a suitable co-oligomerization catalyst at a temperature and time to essentially complete the co-oligomerization reaction.

2. A hydroxyaromatic oligomer composition of claim 1 wherein
   (i) components (A) and (B) are present in quantities which provides from about 0.05 to about 0.55 moles of cyanogen halide or a mixture of cyanogen halides per aromatic hydroxyl group;
   (ii) component (C) is present in quantities which provides from about 0.05 to about 0.6 moles of base per mole of aromatic hydroxyl group; and
   (iii) the mole ratio of epoxy groups to cyanate groups is from about 1:10 to about 1:40.

3. A hydroxyaromatic oligomer composition of claim 2 wherein
   (i) component (A) is a compound represented by formulas I, II or III in the specification;
   (ii) component (B) is cyanogen chloride, cyanogen bromide or a mixture thereof;
   (iii) component (C) is a trialkylamine; and
   (iv) component (D) is represented by formulas IV or V in the specification.

4. A hydroxyaromatic oligomer composition of claim 3 wherein
   (i) component (A) is a compound represented by formula II;
   (ii) component (C) is triethylamine; and
   (iii) component (D) is an epoxy resin represented by formula IV.

5. A hydroxyaromatic oligomer composition of claim 4 wherein
   (i) in component (A) A is a divalent hydrocarbon group having from 1 to about 12 carbon atoms and n has a value of 1; and
   (ii) in component (D) each A is independently a divalent hdyrocarbon group having from 1 to about 12 carbon atoms, n has a value of 1 and $m^2$ has an average value of from about 0 to about 40.

6. A hydroxyaromatic oligomer composition of claim 5 wherein
   (i) in component (A), A is an isopropylidene group; and
   (ii) in component (D) A is an isopropylidene group and $m^2$ has an average value of from about 0.1 to about 20.

7. An epoxy-containing composition having an average of more than one epoxy group per molecule prepared by dehydrohalogenating the reaction product resulting from reacting an epihalohydrin with a hydroxy aromatic oligomer composition containing both triazine and oxazoline groups prepared by reacting (A) at least one material having an average of more than one aromatic hydroxyl group per molecule with (B) at least 0.01 but not more than 0.95 moles of cyanogen halide or mixture of cyanogen halides per aromatic hydroxyl group in the presence of (C) a suitable base in a quantity of from about 0.01 to about 1.1 moles per aromatic hydroxyl group at a temperature and time sufficient to essentially complete the reaction and thereafter recovering the resultant cyanate mixture; (II) co-oligomerizing the product resulting from (I) with (D) an epoxy resin wherein the mole ratio of epoxy groups to cyanate groups is about 1:10 to about 1:100 in the presence of a suitable co-oligomerization catalyst at a temperature and time to essentially complete to co-oligomerization reaction.

8. An epoxy-containing composition of claim 7 wherein
   (i) components (A) and (B) are present in quantities which provides from about 0.05 to about 0.55 moles of cyanogen halide or a mixture of cyanogen halides per aromatic hydroxyl group;
   (ii) component (C) is present in quantities which provides from about 0.05 to about 0.6 moles of base per mole of aromatic hydroxyl group;

(iii) the mole ratio of epoxy groups to cyanate groups is from about 1:10 to about 1:40; and
(iv) said epihalohydrin is epichlorohydrin.

9. An epoxy-containing composition of claim 8 wherein
   (i) component (A) is a compound represented by formulas I, II or III in the specification;
   (ii) component (B) is cyanogen chloride, cyanogen bromide or a mixture thereof;
   (iii) component (C) is a trialkylamine; and
   (iv) component (D) is represented by formulas IV or V in the specification.

10. An epoxy-containing composition of claim 9 wherein
    (i) component (A) is a compound represented by formula II;
    (ii) component (C) is triethylamine; and
    (iii) component (D) is an epoxy resin represented by formula IV.

11. An epoxy-containing composition of claim 4 wherein
    (i) in component (A) A is a divalent hydrocarbon group having from 1 to about 12 carbon atoms and n has a value of 1; and
    (ii) in component (D) each A is independently a divalent hydrocarbon group having from 1 to about 12 carbon atoms, n has a value of 1 and $m^2$ has an average value of from about 0 to about 40.

12. An epoxy-containing composition of claim 5 wherein
    (i) in component (A), A is an isopropylidene group; and
    (ii) in component (D) A is an isopropylidene group and $m^2$ has an average value of from about 0.1 to about 20.

13. A product resulting from curing an epoxy-containing composition of claim 7 with a curing quantity of a suitable catalyst and/or curing agent.

14. A product resulting from curing an epoxy-containing composition of claim 8 with a curing quantity of a suitable catalyst and/or curing agent.

15. A product resulting from curing an epoxy-containing composition of claim 9 with a curing quantity of a suitable catalyst and/or a curing agent.

16. A product resulting from curing an epoxy-containing composition of claim 10 with a curing quantity of a suitable catalyst and/or curing agent.

17. A product resulting from curing an epoxy-containing composition of claim 11 with a curing quantity of a suitable catalyst and/or curing agent.

18. A product resulting from curing an epoxy-containing composition of claim 12 with a curing quantity of a suitable catalyst and/or curing agent.

* * * * *

UNITED STATES PATENT AND TRADEMARK OFFICE
CERTIFICATE OF CORRECTION

PATENT NO. : 4,487,915

DATED : December 11, 1984

INVENTOR(S) : Robert E. Hefner, Jr.

It is certified that error appears in the above—identified patent and that said Letters Patent is hereby corrected as shown below:

Col. 1, line 33; change "ex-" to --e- --.

Col. 2, line 46; change "resin" to --resins--.

Cols. 2, 3, 4 & 5, in all the formulas; the rings should indicate that they are aromatic rings by placing a large circle inside the ring so that each ring appears as follows:

Col. 4, line 16; change "3,3',5,5'tetra-" to --3,3',5,5'-tetra- --.

Col. 4, line 17; change "chloro-4,4'dihydroxydiphenyl" to --chloro-4,4'-dihydroxydiphenyl--.

Col. 4, line 46; insert a comma --,-- after "amines".

Col. 5, line 29; change "the" to --an--.

UNITED STATES PATENT AND TRADEMARK OFFICE
CERTIFICATE OF CORRECTION

PATENT NO. : 4,487,915

DATED : December 11, 1984

INVENTOR(S) : Robert E. Hefner, Jr.

It is certified that error appears in the above—identified patent and that said Letters Patent is hereby corrected as shown below:

Col. 7, line 16; change "nd" to --and--.

Col. 7, line 43; change "additonal" to --additional--.

Col. 7, line 46; change "vaccuum" to --vacuum--.

Col. 8, line 8; change "impact" to --Impact--.

Col. 8, line 9; change "method" to --methods--.

Col. 10, line 67; insert --percent-- between "area" and "Bisphenol".

Col. 12, line 28, Claim 4; change "hdyrocarbon" to --hydrocarbon--.

Col. 12, line 58, Claim 7; change "to" to --the--.

Col. 14, line 18, Claim 15; delete the second occurrence of "a".

Signed and Sealed this

Twenty-first Day of May 1985

[SEAL]

Attest:

DONALD J. QUIGG

Attesting Officer

Acting Commissioner of Patents and Trademarks